US00PP28639P3

(12) United States Plant Patent
Kobayashi

(10) Patent No.: US PP28,639 P3
(45) Date of Patent: Nov. 14, 2017

(54) POINSETTIA PLANT NAMED 'PER35_11'

(50) Latin Name: ***Euphorbia*×hybrid**
Varietal Denomination: PER35_11

(71) Applicant: DUMMEN GROUP B.V., De Lier (NL)

(72) Inventor: Ruth Kobayashi, Carlsbad, CA (US)

(73) Assignee: Dümmer Group B.V., De Lier (NL)

( * ) Notice: Subject to any disclaimer, the term of this patent is extended or adjusted under 35 U.S.C. 154(b) by 102 days.

(21) Appl. No.: 14/998,481

(22) Filed: Jan. 9, 2016

(65) Prior Publication Data

US 2017/0202124 P1 Jul. 13, 2017

(51) Int. Cl.
*A01H 5/02* (2006.01)

(52) U.S. Cl.
USPC ..... Plt./303

(58) Field of Classification Search
USPC ..... Plt./263.1, 302, 303
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER35_11', characterized by its uniform, upright and mounded plant habit; vigorous growth habit; freely branching habit; dark green-colored leaves; inflorescences with bright red purple-colored flower bracts with white-colored margins; and good post-production longevity.

2 Drawing Sheets

Botanical designation: *Euphorbia*×hybrid.
Cultivar denomination: 'PER35_11'.

CROSS-REFERENCED TO CLOSELY RELATED APPLICATIONS

Title: Poinsettia Plant Named 'PER35_11'
Applicant: Ruth Kobayashi
Filed: Jan. 9, 2016, concurrently with this application Ser. No. 14/998,482

BACKGROUND OF THE INVENTION

The present invention relates to a new and distinct cultivar of Poinsettia plant, botanically known as *Euphorbia*×hybrid, and hereinafter referred to by the name 'PER35_11'.

The new Poinsettia plant is a product of a planned breeding program conducted by the Inventor in Encinitas, Calif. The objective of the breeding program is to create new uniform Poinsettia plants having inflorescences with numerous attractive flower bracts and excellent post-production longevity.

The new Poinsettia plant is a naturally-occurring whole plant mutation of *Euphorbia*×hybrid 'PERHC59B', disclosed in U.S. Plant Pat. No. 24,158. The new Poinsettia plant was discovered and selected by the Inventor as a single flowering plant from within a population of plants of 'PERHC59B' in a controlled greenhouse environment in Encinitas, Calif. on Dec. 2, 2010.

Asexual reproduction of the new Poinsettia plant by terminal vegetative cuttings in a controlled greenhouse environment in Encinitas, Calif. since January, 2011 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER35_11'. These characteristics in combination distinguish 'PER35_11' as a new and distinct Poinsettia plant:

1. Uniform, upright and mounded plant habit.
2. Vigorous growth habit.
3. Freely branching habit.
4. Dark green-colored leaves.
5. Under natural season conditions, plants flower in mid-November in Southern California.
6. Inflorescences with bright red purple-colored flower bracts with white-colored margins.
7. Good post-production longevity.

Plants of the new Poinsettia differ primarily from plants of the mutation parent, 'PERHC59B', in flower bract color as flower bracts of plants of 'PERHC59B' are hot pink in color with light pink-colored margins.

Plants of the new Poinsettia differ primarily from plants of *Euphorbia*×hybrid, 'PER12_11', in flower bract color as flower bracts of plants of 'PER12_11' are pale pink in color. In addition, plants of the new Poinsettia are more vigorous than plants of 'PER12_11'.

Plants of the new Poinsettia can be compared to plants of the *Euphorbia*×hybrid 'PERHC18B', not patented. In side-by-side comparisons conducted in Encinitas, Calif., plants of the new Poinsettia differed primarily from plants of 'PERHC18B' in the following characteristics:

1. Plants of the new Poinsettia were more vigorous than plants of 'PERHC18B'.
2. Plants of the new Poinsettia were male and female sterile whereas plants of 'PERHC18B' were male fertile and female sterile.

3. Plants of the new Poinsettia and 'PERCH18B' differed in flower bract color as flower bracts of plants of 'PERHC18B' were medium pink in color.

Plants of the new Poinsettia can also be compared to plants of the *Euphorbia* 'Princettia Hot Pink', not patented. In side-by-side comparisons conducted in Encinitas, Calif., plants of the new Poinsettia differed primarily from plants of 'Princettia Hot Pink' in the following characteristics:

1. Plants of the new Poinsettia were more vigorous than plants of 'Princettia Hot Pink'.
2. Plants of the new Poinsettia were more upright than and not as mounding as plants of 'Princettia Hot Pink'.
3. Plants of the new Poinsettia and 'Princettia Hot Pink' differed in flower bract color as flower bracts of plants of 'Princettia Hot Pink' were hot pink in color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'PER35_11' grown in a container.

The photograph on the second sheet is a close-up view of a typical flowering plant of 'PER35_11'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 25 weeks old when the photographs and the description were taken. In the following description, color references are made to The Royal Horticultural Society Colour Chart, 2007 Edition, except where general terms of ordinary dictionary significance are used.

Botanical classification: *Euphorbia*×hybrid 'PER35_11'.

Parentage: Naturally-occurring whole plant mutation of *Euphorbia*×hybrid 'PERHC59B', disclosed in U.S. Plant Pat. No. 24,158.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; typically white in color, actual color of the roots is dependent on substrate composition, water quality, fertilizer type and formulation, substrate temperature and physiological age of roots.

Plant description:

*Plant habit and form.*—Uniform, upright and mounded plant habit; inverted triangle; large branched inflorescences positioned above the foliar plane; vigorous growth habit.

*Plant height.*—About 36 cm.

*Plant diameter or spread.*—About 47 cm.

*Lateral branch description.*—Quantity: Freely branching habit, about seven lateral branches develop after pinching. Length: About 32 cm. Diameter: Thick, about 7.5 mm to 8 mm. Internode length: About 1.7 cm to 2.3 cm. Strength: Strong. Texture: Smooth, glabrous. Luster: Moderately glossy. Color: Close to between 144A and 146A.

*Leaf description.*—Arrangement: Alternate, simple. Length: About 11 cm. Width: About 6 cm. Shape: Narrowly ovate to elliptical. Apex: Acuminate. Base: Obtuse with cuneate tendencies. Margin: Entire; undulate. Aspect: Mostly horizontal to slightly upright. Texture, upper surface: Smooth, glabrous; velvety. Texture, lower surface: Glabrous; prominent venation. Luster, upper and lower surfaces: Matte. Venation pattern: Pinnate, arcuate. Color: Developing and fully expanded leaves, upper surface: Darker green than between N137A and 147A; venation, close to 146A to 146B. Developing and fully expanded leaves, lower surface: Close to 147B; venation, close to 146B to 146C. Leaf petioles: Length: About 4.8 cm. Diameter: About 4 mm. Texture, upper and lower surfaces: Smooth, glabrous. Luster, upper and lower surfaces: Somewhat glossy. Color, upper surface: Close to 146A to 146B. Color, lower surface: Close to 146B to 146C.

Inflorescence description:

*Inflorescence type and habit.*—Inflorescences are compound corymbs of cyathia with colored flower bracts subtending the cyathia; inflorescences positioned above the foliar plane.

*Quantity of inflorescence.*—One inflorescence develops per lateral branch; inflorescences typically are divided into three parts.

*Fragrance.*—None detected.

*Flowering response.*—Under natural season conditions, plants typically flower in mid-November in Southern California; under artificial long nyctoperiod/short photoperiod conditions, plants flower about seven to eight weeks later.

*Post-production longevity.*—Good post-production longevity; plants of the new Poinsettia maintain good substance and flower bract color for about four to six weeks under interior conditions; inflorescences persistent.

*Inflorescence size.*—Diameter, per inflorescence division: About 16 cm. Height (depth): About 6 cm.

*Flower bracts.*—Quantity per inflorescence division: About 15 to 18. Length, largest bracts: About 9.25 cm. Width, largest bracts: About 4.25 cm. Shape: Narrowly ovate to elliptical. Apex: Acuminate. Base: Obtuse with cuneate tendencies. Margin: Mostly entire; slightly undulate. Aspect: Initially upright and becoming closer to horizontal with development. Texture, upper surface: Smooth, glabrous; velvety. Texture, lower surface: Glabrous; prominent venation. Luster, upper and lower surfaces: Matte. Venation pattern: Pinnate, arcuate. Color: Developing or transitional bracts, upper surface: Ground color, brighter green than 146A; irregular and random interveinal sectors, close to N57B, 61B, 61C, 155C and 155D. Developing or transitional bracts, lower surface: Ground color, close to 144A; irregular and random interveinal sectors, close to 155D. Fully expanded bracts, upper surface: Close to N57A to more intense than N57A; thin margins, close to NN155D; color does not fade with development. Fully expanded bracts, lower surface: Close to 155C to 155D; color from upper surface, close to N57B, showing through; color does not fade with development. Bract petioles: Length: About 2 cm. Diameter: About 2.5 mm. Texture, upper and lower surfaces: Smooth, glabrous. Luster, upper and lower surfaces: Moderately glossy. Color, upper and lower surfaces: Close to 144A to 144B.

*Cyathia.*—Rudimentary cyathia have been observed, however they do not develop stamens nor pistils and typically abscise as the flower bracts develop color. Quantity per inflorescence division: About 15 to 18. Length: About 3 mm. Width: About 2.5 mm. Shape: Round. Color: Close to N144A.

*Nectaries.*—None observed.

*Peduncles.*—Length: About 1 mm. Diameter: About 1 mm. Strength: Strong. Aspect: Upright to outwardly. Texture: Smooth, glabrous. Color: Close to N144A.

*Reproductive organs.*—Stamens: Cyathia of plants of the new Poinsettia have not been observed to develop stamens. Pistils: Cyathia of plants of the new Poinsettia have not been observed to develop pistils.

*Seeds and fruits.*—Seed and fruit production has not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER35_11' as illustrated and described.

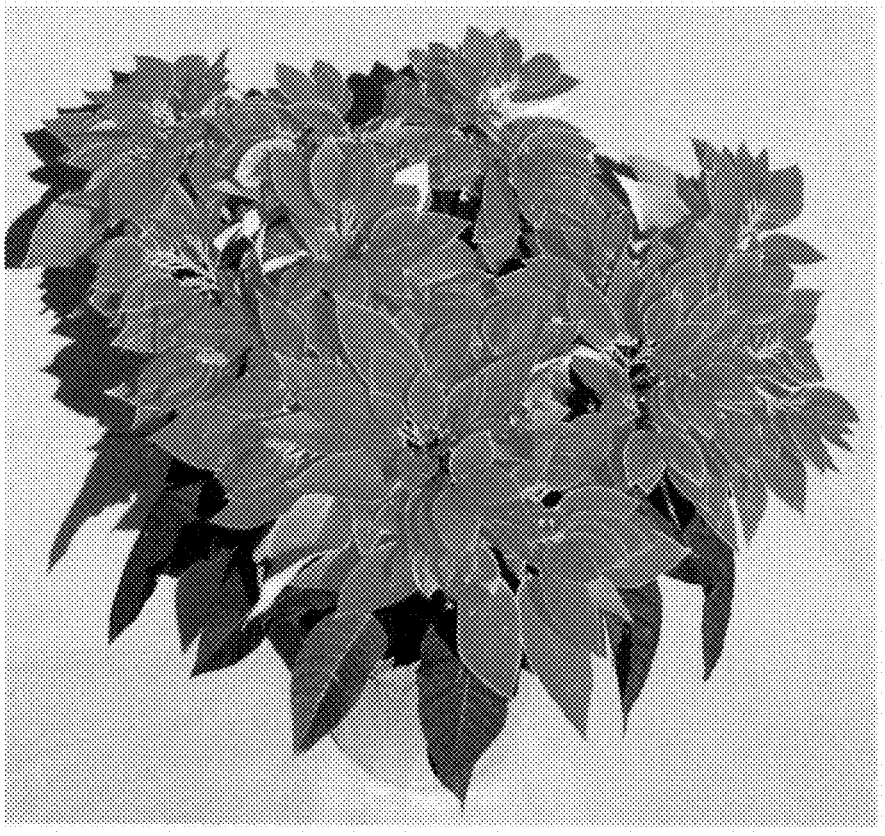

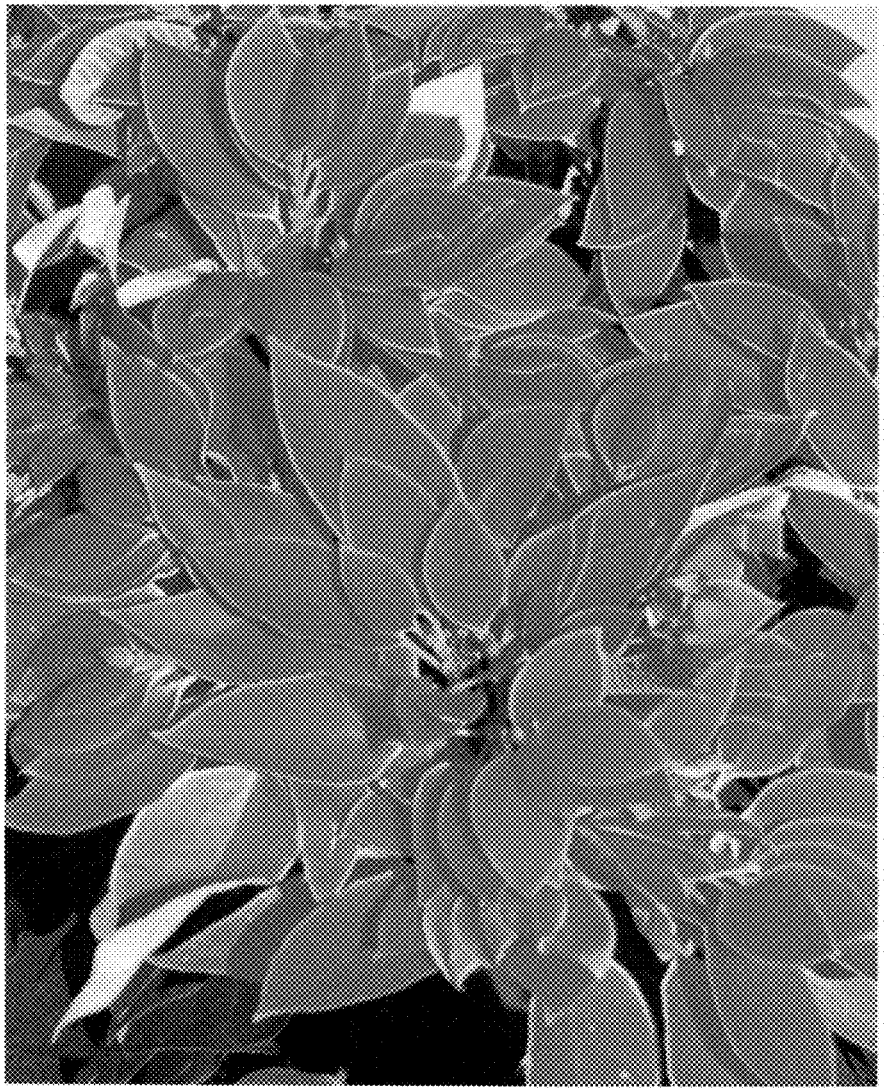

* * * * *